United States Patent [19]

Mehlhorn et al.

[11] Patent Number: 4,837,216

[45] Date of Patent: Jun. 6, 1989

[54] AGENTS AGAINST PROTOZOA IN INSECTS

[75] Inventors: Heinz Mehlhorn, Neuss-Üdesheim; Günter Schmahl, Bochum, both of Fed. Rep. of Germany

[73] Assignee: Bayer Aktiengesellschaft, Leverkusen, Fed. Rep. of Germany

[21] Appl. No.: 148,814

[22] Filed: Jan. 27, 1988

[30] Foreign Application Priority Data

Feb. 3, 1987 [DE] Fed. Rep. of Germany ....... 3703105

[51] Int. Cl.⁴ .............................................. A01N 43/66

[52] U.S. Cl. .................................................. 514/241

[58] Field of Search ........................................ 514/241

[56] References Cited

U.S. PATENT DOCUMENTS 3,970,752 7/1976 Aichinger et al. .................. 514/241

4,219,552 8/1980 Haberkorn et al. ................. 514/241

FOREIGN PATENT DOCUMENTS 3300793 7/1984 Fed. Rep. of Germany .

3408768 9/1985 Fed. Rep. of Germany .

*Primary Examiner*—Allen J. Robinson

*Assistant Examiner*—Raymond J. Henley, III

*Attorney, Agent, or Firm*—Sprung Horn Kramer & Woods

[57] ABSTRACT

A method of combating protozoa in insects which comprises applying to such insects or to an insect habitat an amount effective therefor of a triazinetrione of the formula

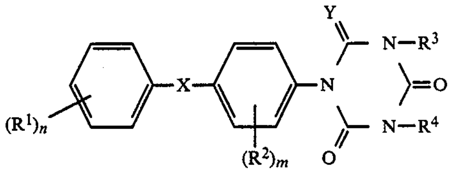

(I)

in which

X is 0 or S,

Y is 0 or S, $R^1$ and $R^2$ each independently is a radical from the group consisting of halogen, nitro, CN, amino, alkyl, halogenoalkyl, alkoxy, halogenoalkoxy, alkylthio, haogenoalkylthio, alkylsulphonyl, alkylsulphinyl, halogenoalkylsulphonyl, halogenoalkylsulphinyl, acyl, carboxy, carbonylamino, carbonylalkoxy, carbamoyl and sulphamoyl, n and m each independently is an integer from 0 to 3, and $R^3$ and $R^4$ each independently is hydrogen or alkyl.

5 Claims, No Drawings

AGENTS AGAINST PROTOZOA IN INSECTS

The present invention relates to the use of known triazinetriones as agents against protozoa in insects.

The protozoa include parasites which are widespread in insects (for example *Nosema apis* in bees). Stock insects kept by humans (for example bees or silkworms), and also insects bred in the laboratory and insects living in the open are affected by these. The parasites damage the host animals by destroying their organs. Together with other parasites (for example Varomites in bees), they can cause considerable damage to the host animals and this can lead to their death. In honey bees, they cause considerable damage by reducing honey production and by a weakening and dying of the population. In laboratory breeding of insects which are kept to collect genetic material and maintain species, only a few animals are often available, and valuable information is lost with their death.

There are as yet no agents against protozoa in insects.

It has been found that the known triazinetriones of the formula (I)

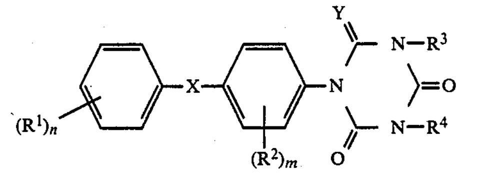

(I)

in which

X represents O or S,

Y represents O or S, the symbols $R^1$ represent identical or different radicals from the group comprising halogen, nitro, CN, amino, alkyl, halogenoalkyl, alkoxy, halogenoalkoxy, alkylthio, halogenoalkylthio, alkylsulphonyl, alkylsulphinyl, halogenoalkylsulphonyl, halogenoalkylsulphinyl, acyl, carboxy, carbonylamino, carbonylalkoxy, carbamoyl and sulphamoyl, the symbols $R^2$ represent identical or different radicals from the group of substituents given for $R^1$, n and m represent integers from 0 to 3, $R^3$ represents hydrogen or alkyl and $R^4$ represents hydrogen or alkyl, can be used for combating protozoa in insects.

The compounds of the formula (I) are known or can be prepared by methods which are known per se (DE-OS (German Published Specification) No. 2,413,722; DE-OS (German Published Specification) No. 2,718,799 and U.S. Pat. No. 4,219,552).

Preferred compounds of the formula: (I) are those in which

X and Y represent O $R^1$ and $R^2$ independently of one another represent identical or different radicals from the group comprising halogen, in particular fluorine, chlorine or bromine, nitro, CN, amino, $C_{1-4}$-alkyl, in particular methyl or ethyl, $C_{1-4}$-halogenoalkyl, in particular trifluoromethyl, trichloromethyl or fluoro-chloroethyl, $C_{1-4}$-alkoxy, in particular methylenedioxy, isopropoxy or methoxy, $C_{1-4}$-halogenoalkoxy, in particular trifluoromethoxy, difluoromethylenedioxy or tetrafluoroethylenedioxy, $C_{1-4}$-alkylthio, in particular methylmercapto or ethylmercapto, $C_{1-4}$-halogenoalkylthio, in particular trifluoromethylthio, $C_{1-4}$-alkylsulphonyl, in particular methylsulphonyl, $C_{1-4}$-alkylsulphinyl, $C_{1-4}$-halogenoakylsulphonyl and -sulphinyl, in particular trifluoromethylsulphonyl, $C_{1-4}$-acyl, in particular acetyl, propionyl or benzoyl, and $C_{1-4}$-carbonylalkoxy, in particular methoxycarbonyl or ethoxycarbonyl, n and m represent integers from 0 to 2 and $R^3$ and $R^4$ independently of one another represent hydrogen or $C_{1-4}$-alkyl, in particular methyl.

Compounds of the formula (I) which are particularly preferably employed are those in which $R^4$ represents hydrogen, $R^3$ represents $C_{1-4}$-alkyl, Y represents oxygen or sulphur, X represents oxygen, the symbols $R^2$ represent identical or different radicals from the group comprising $C_{1-4}$-alkyl, halogen, such as, in particular, chlorine or bromine, $C_{1-4}$-alkoxy and $C_{1-2}$-halogenoalkyl, the symbols $R^1$ represent identical or different radicals from the group comprising halogen, in particular chlorine or bromine, $NO_2$, $C_{1-4}$-alkyl, $C_{1-2}$-halogenoalkyl, $C_{1-4}$-alkylmercapto, which is optionally substituted by halogen, $C_{1-4}$-alkoxy, which is optionally substituted by halogen, $C_{1-4}$-alkylsulphinyl, which is optionally substituted by halogen, and $C_{1-4}$-alkylsulphonyl, which is optionally substituted by halogen, and n and m represent integers from 0 to 2.

Particularly preferred compounds of the formula (I) are those in which $R^4$ represents hydrogen, $R^3$ represents methyl, X and Y represent oxygen, the symbols $R^2$ represents a radical from the group comprising chlorine, bromine, methyl, trifluoromethyl, methoxy and ethoxy, the symbols $R^1$ represents a radical in particular in the 4-position, from the group comprising trifluoromethylmercapto, trifluoromethylsulphinyl, trifluoromethylsulphonyl and trifluoromethoxy and n and m independently of one another represent 0 or 1.

The following compounds may be mentioned as examples without limiting the invention in any way: 1-[3,5-dichloro-4-(4'-trifluoromethoxy-phenoxy)-phenyl]-3-methyl-1,3,5-triazine-2,4,6(1H,3H,5H)-trione, 1-[3,5-dichloro-4-(4'-trifluoromethylthio-phenoxy)-phenyl]-3-methyl-1,3,5-triazine-2,4,6(1H,3H,5H)-trione, 1-[4-(4'-trifluoromethylthio-phenoxy)-phenyl]]-3-methyl-1,3,5-triazine-2,4,6(1H,3H,5H)-trione, 1-[3-chloro-5-bromo-4(4'-trifluoromethylthio-phenoxy)-phenyl]-3-methyl-1,3,5-triazine-2,4,6(1H,3H,5H)-trione, 1-[3,5-dibromo-4-(4'-trifluoromethylthio-phenoxy)-phenyl]-3-methyl-1,3,5-triazine-2,4,6(1H,3H,5H)-trione, 1-[3,5-dichloro-4-(3'-methyl-4'-trifluoromethylthio-phenoxy)-phenyl]-3-methyl-1,3,5-triazine-2,4,6(1H,3H,5H)-trione, 1-[4-(4'-tri-fluoromethylsulphonyl-phenoxy)-phenyl]-3-methyl-1,3,5-triazine-2,4,6(1H,3H,5H)-trione, 1-[3,5-dichloro-4-(4'-trifluoromethylsulphonyl-phenoxy)-phenyl]-3-methyl-1,3,5-triazine-2,4,6(1H,3H,5H)-trione, 1-[3-chloro-5-bromo-4-(4'-trifluoromethylsulphonyl-phenoxy)-phenyl]-3-methyl-1,3,5-triazine-2,4,6(1H,3H,5H)-trione, 1-[3,5-dichloro-4-(2'-chloro-4'-trifluoromethylsulphonyl-phenoxy)-phenyl]3-methyl-1,3,5-triazine-2,4,6(1H,3H,5H)-trione, 1-[3-methoxy-4-(4'-trifluoromethylthio-phenoxy)-phenyl]-3-methyl-1,3,5-triazine-2,4,6-(1H,3H,5H)-trione, 1-[4-(4'-trifluoromethylsulphinyl-phenoxy)-phenyl]-3-methyl-1,3,5-triazine-2,4,6(1H,3H,5H)-trione, 1-[3,5-dichloro-4-(4'-trifluoromethylsulphinyl-phenoxy)-phenyl]-3-methyl-1,3,5-triazine-2,4,6(1H,3H,5H)-trione, 1-[4-(3'-trifluoromethylsulphonyl-phenoxy)-3,5-dimethylphenyl]-3-methyl-1,3,5-triazine-2,4,6(1H,3H,5H)-trione, 1-[3-chloro-4-(4' -trifluoromethylsulphonyl-phenoxy)-phenyl]-3-methyl-1,3,5-triazine-2,4,6(1H,3H,5H)-trione, 1-[3-methyl-4-(4'-trifluoromethylthio-phenoxy)-phenyl]-3-methyl-1,3,5-triazine-2,4,6(1H,3H,5H)-trione, 1-[3,5-dichloro-4-(2'-methyl-4'-trifluoromethylsulphonyl-phenoxy)-phenyl]-3-methyl-1,3,5-triazine-2,4,6(1H,3H,5H)-trione, 1-[3-chloro-5-methyl-4-(2'-chloro-4'-trifluoromethylsulphonyl-phenoxy)-phenyl]-3-methyl-1,3,5-triazine-2,4,6(1H,3H,5H)-trione, 1-[4-(4'-trifluoromethylsulphonyl-phenoxy)-3,5-dimethyl-phenyl]-3-methyl-1,3,5-triazine-2,4,6(1H,3H,5H)-trione, 1-[3-chloro-5-methyl-4-(4'-trifluoromethylsulphonyl-phenoxy)phenyl]-3-methyl-1,3,5-triazine-2,4,6(1H,3H,5H)-trione, 1-[3-chloro-4-(2'-chloro-4'-trifluoromethylthio-phenoxy)-phenyl]-3-methyl-1,3,5-triazine-2,4,6(1H,3H,5H)-trione, 1-[3-bromo-4-(4'-trifluoromethylsulphonyl-phenoxy)-phenyl-]-3-methyl-1,3,5-triazine-2,4,6(1H,3H,5H)-trione, 1-[3-chloro-5-trifluoromethyl-4-(4'-trifluoromethylsulphonyl-phenoxy)-phenyl]-3-methyl-1,3,5-triazine-2,4,6(1H,3H,5H)trione, 1-[3,5-dichloro-4(4'-trifluoromethylsulphonyl-phenoxy)-phenyl]-3-methyl-2-thioxo-4,6-dioxo-1,3,5(1H,3H,5H)-triazine, 1-[3-methyl-4-(4'-trifluoromethylthio-phenoxy)phenyl-]-3-methyl-2-thioxo-4,6-dioxo-1,3,5-(1H, 3H,5H)-triazine and 1-[3-methyl-4-(6-trifluoromethylbenzothiazol-2-yloxy)-phenyl]-3-methyl-1,3,5-triazine-2,4,6(1H,3H,5H)-trione.

Toltrazuril, the common name for 1-[3-methyl-4-(4'-trifluoromethylthio-phenoxy)-phenyl]-3-methyl-1,3,5-triazine-2,4,6(1H,3H,5H)-trione, may be particularly singled out.

It was known that the triazinetriones of the formula (I) can be used for combating Coccidiae in mammals and poultry. Nothing was known of the fact that they can also be used for combating protozoa in insects. This was also not to be expected, since this use is also unknown for other coccidiosis agents.

The protozoa which occur as parasites in insects include the pests of the strain Microsporida, in particular of the genus Nosema. *Nosema apis* may be mentioned in particular.

The insects include the stock and breeding insects kept by humans, such as, for example, honey bees, silkworms and hymenopters, as well as all the insects kept in laboratory breeds which are kept either for experimental purposes or for collection of genetic material.

The compounds of the formula (I) can be used on all the development stages of the insects.

The treatment can also be carried out with agents which, in addition to the active compounds mentioned, contain active compounds against other pests. Thus, in the case of bees, for example, combined treatment against Nosema and *Varroa jacobsoni* is possible if the agents contain, in addition to the active compounds mentioned, for example synthetic phosphoric acid esters, such as coumaphos or malathion, formamidines, such as chlordimeform, phenothiazines, such as promazine, synthetic pyrethroids, such as flumethrin, cyfluthrin, cyhalothrin or amitraz, or cymiazole.

The protozoa on the insects can be treated in various ways:

1. By direct contact with the active compound. Here, for example, this is sprayed, dusted, smoked, vaporized, evaporated or incorporated into carriers which come into contact with the insects, or applied to the carriers,
2. By a systemic action via the haemolymphs of the insects. Here, the active compound is provided, for example, with the food or drinking water or in the case of insects which form populations, is poured or sprayed into the hive.

The treatment can in principle take place throughout the entire year.

Since protozoa occur to an increased extent in the warm season, treatment at the start of the warm season is particularly preferred.

If the active compound is vaporized or evaporated or incorporated into carriers, treatment is preferably carried out throughout the entire year.

In the case of honey bees, the treatment is particularly advantageously carried out at the time of winter feeding or in the period with no breeding.

In the case of honey bees, the bee population can furthermore be treated as an artificial swarm. This can also be effected during the breeding period.

Agents which are sprayed contain the active compound in concentrations of 0.1–50% by weight, preferably 0.3–20% by weight.

These agents are used either directly or after further dilution, preferably with water. In the case of direct use of the agents, application by the ultra-low volume (ULV) process with the customary equipment suitable for this is preferred. The agents can also be sprayed with the aid of electrostatic charging.

Before use, the agents can be diluted to active compound concentrations of $10^{-4}-2\%$ by weight, preferably $10^{-3}-0.5\%$ by weight. They are sprayed conventionally with the customary equipment, such as back sprays, piston pumps and lacquering guns.

Either the insects or their habitat or parts thereof or their environment are treated with these agents.

The agents contain the active compound in addition to diluents and/or emulsifiers which are tolerated by the insects in the concentrations used.

Suitable diluents are water, alcohols, such as methanol, ethyl alcohol, propanol, isopropyl alcohol, n-butyl alcohol, amyl alcohol and octanol; glycols, such as propylene glycol, 1,3-butylene glycol, ethylene glycol and dipropylene glycol monomethyl ether; diethylene glycol monomethyl ether; glycerol; aromatic alcohols, such as benzyl alcohol; carboxylic acid esters, such as, for example, ethyl acetate, benzyl benzoate, butyl acetate, propylene carbonate and ethyl lactate; aliphatic hydrocarbons and oils, such as, for example, cottonseed oil, peanut oil, oorn oil, olive oil, castor oil and sesame oil; ketones, such as, for example, acetone and methyl ethyl ketone; and synthetic mono- and triglycerides with naturally occurring fatty acids.

Inter alia, compounds such as dimethyl sulphoxide, dimethylacetamide, dimethylformamide, N-methypyrolidone, dioxane and 2-dimethyl-4-oxymethyl-1,3-dioxalane are furthermore particularly suitable as diluents.

Water and lower alcohols with up to 8 carbon atoms in the molecule, as well as lower ketones, such as methyl ethyl ketone, and ethers of ethylene glycol and of propylene glycol, are especially suitable.

One or more diluents can be employed for the preparation of the agents which can be used according to the invention.

Suitable emulsifiers are: anionic surfactants, such as Na laurylsulphate, fatty alcohol ether-sulphates, mono/dialkylpolyglycol ether-orthophosphate monoethanolamine saltsand calcium alkylarylsulphonates cationic surfactants, such as cetyltrimethylammonium chloride, ampholytic surfactants, such as di-Na N-lauryl-β-iminodipropionate or lecithin, non-ionic surfactants, for example polyoxyethylated castor oil, polyoxyethylated sorbitan monooleate or sorbitan monostearate and glycerol monostearate, polyoxyethylene stearate or alkylphenol polyglycol ethers.

Preferred emulsifiers which may be mentioned are: non-ionic water-soluble emulsifiers with an HLB (hydrophilic/lipophilic balance value) of greater than 10, for example Emulgator NP 10® (Bayer AG), an alkylaryl polyglycol ether; Renex 678® (Atlas Chemical Industries), a polyoxyethylene alkylaryl ether; Tween 40® (Atlas), polyoxyethylene sorbitan monopalmitate 53® (Atlas), polyoxyethylene stearate; Atlas G 3707®, polyoxyethylene lauryl ether; Atlas G 3920®, polyoxyethylene oleyl ether; Atlas G 9046 T®, polyoxyethylene mannitan-monolaurate; Emulgator 1371 B® (Bayer AG), an alkylpolyglycol ether; Emulgator 16736® (Bayer AG), an alkylpolyglycol ether (oleylpolyglycol ether); Emulgator OX® (Bayer AG), an alkylpolyglycol ether (dodecylpolyglycol ether); Ninox BM-2® (Stepan Chemical Co.), ethoxylated nonylphenol; Triton X-100® (Rohm and Haas Co.), isooctylphenolpoly- ethoxyethanol; and Cremophor EL®, polyoxyethylated castor oil.

The agents according to the invention contain the emulsifiers in concentrations of up to 10 times, preferably up to 5 times, that of the active compound employed. The diluents are in each case added to make up the desired end concentration.

The agents are prepared by dissolving the active compound or compounds in the solvent or in an emulsifier or emulsifier-solvent mixture, if necessary with warming. Further dilution of the agents with water to the desired concentration is carried out if necessary.

The agents for dusting contain the active compound in addition to conventional carriers which are tolerated by insects and are suitable for the preparation of powders or wettable powders.

Suitable carriers are inorganic carriers, such as, for example, talc, kaolin, calcium carbonate, silicates and bentonites, and furthermore organic carriers, such as, for example, starches, for example rice starch, sugar, cellulose and cellulose derivatives.

The agents are prepared by mixing the active compound or compounds with the carriers, if appropriate with the addition of wetting agents. Suitable wetting agents are, for example, the emulsifiers mentioned above.

Agents which are smoked contain the active compound in concentrations of $10^{-7}$ –2% by weight per 100 g of carrier material. The customary material for smoker preparations is used as the carrier material.

Agents through which the active compound is vaporized are, for example, carrier materials which are impregnated with agents containing the active compound, or into which the active compound is incorporated. Leaves or films of paper, card, cellulose, fabric, felt, fleece or leather which are impregnated with agents containing the active compound and can be heated, for example, by a heat source are preferred. The small electric or battery-operated vaporizer ovens customary for vaporizer leaves may be mentioned as the heat source.

It is particularly advantageous to employ agents into which the active compound is incorporated or onto which it is applied and which act without an additional heat source. The treatment can then be carried out particularly easily. The agents are simply introduced into the habitat of the insects.

The treatment is ended by removing the agent. This prevents the parasites from being exposed to continuously decreasing concentrations of active compound. Resistance development in the parasites is thereby prevented.

The long-lasting release of active compound from these agents allows long-term therapy, which also affects the offspring from the breeding of the insects.

The active compound in these agents can be contained in or incorporated into carriers or can be applied in a suitable form to carriers.

Carriers are shaped articles which are introduced onto or into the habitat of the insects. It is also possible for parts of the habitat to be shaped from material into which the active compound is incorporated or onto the surface of which the active compound is applied, or which is soaked or impregnated with the active compound. In the case of bees, for example, partitions which are inserted between the honeycombs and have been treated with agents containing the active compound or into which the active compound is incorporated are preferred.

Carriers which can be used are naturally occurring or synthetic carriers. Naturally occurring carriers are, for example, wood, processed wood products, card, paper, gum, rubber, felt, metal, glass, porcelain and ceramic materials. Synthetic carriers are, for example, plastics based on polyvinyl, PVC, polyacrylate, polymethacrylate, epoxide, polyurethane, polyester, polyamide, cellulose and derivatives thereof, polyethylene, polypropylene and synthetic rubber.

Layers applied to a solid or flexible substrate are also possible carriers. Such layers can be absorbent and can be treated with agents containing the active compound. However, they can also be non-absorbent and contain incorporated active compound. As a rule these layers are adhesive polymers to which, if appropriate, inert filler substances are added. The polymers used here are the lacquer raw materials of the paint industry and, for example, cellulose derivatives, acrylates and methacrylates.

Examples which may be mentioned of fillers for the preparation of absorbent layers are: kaolin, calcium carbonate, silicates, bentonites, cellulose, cellulose derivatives, starch and wood powder. The active compound here is either already incorporated into the layer-forming material, or the layer is subsequently soaked or impregnated or sprayed, for example with the above-mentioned agents to be sprayed.

Layers which contain incorporated active compound can also be formed by paint films or lacquers containing the active compound. These contain the active compound in a concentration of 0.00001–10, preferably 0.001–1% by weight, in addition to the customary coating base. Dispersion paint films and lacquers are preferably used as the coating base.

Layers which contain incorporated active compound can also be, however, films, strips and tapes which are single- or multi-layered and if appropriate self-adhesive.

Thus, a self-adhesive film containing the active compound can consist, for example, of an adhesive layer, a flexible carrier layer, a flexible carrier layer containing the active compound and a flexible covering layer free from the active compound. The individual layers consist of polymer materials which are known per se and are suitable for the preparation of such layers.

As already mentioned, these shaped articles can contain incorporated active compound. They contain the active compound in concentrations of 0.00001–10% by weight, preferably 0.00001–1% by weight, based on the basic material of the shaped article.

Suitable shaped articles are strips, tapes, sheets and also, as mentioned above, structural components.

Polyvinyl resins, polyacrylates, epoxy resins, cellulose, cellulose derivatives, polyamides and polyesters which are sufficiently compatible with the abovementioned active compounds can be used to produce the shaped articles according to the invention. The polymers must have a sufficient strength and flexibility so that they do not tear or become fragile during shaping. They must permit sufficient migration of the active compounds at the surface of the shaped article.

Examples of typical vinyl resins are polyvinyl halides, such as polyvinyl chloride, polyvinyl chloridevinyl acetate and polyvinyl fluoride; polyacrylates and polymethacrylates, such as polymethyl acrylate and polymethyl methacrylate; and polyvinylbenzenes, such as polystyrene and polyvinyltoluene.

The plasticizers which are usually employed for plasticizing solid vinyl resins are suitable for production of the shaped articles according to the invention which are based on polyvinyl resin. The plasticizer used depends on the resin and its compatibility with the plasticizer. Examples of suitable plasticizers are esters of phosphoric acid, such as tricresyl phosphate, esters of phthalic acid, such as dimethyl phthalate and dioctyl phthalate, and esters of adipic acid, such as diisobutyl adipate. It is also possible for other esters, such as the esters of azelaic acid, maleic acid, ricinoleic acid, myristic acid, palmitic acid, oleic acid, sebacic acid, stearic acid and trimellitic acid, as well as complex linear polyesters, polymeric plasticizers and epoxidized soybean oils to be used. The amount of plasticizer is about 10 to 50% by weight, preferably about 20 to 45% by weight of the total composition.

The shaped articles can also contain further constituents, such as stabilizers, lubricants, fillers and colouring materials, without the fundamental properties of the composition thereby being modified. Suitable stabilizers are antioxidants and agents which protect the shaped articles from ultraviolet radiation and undesirable degradation during working, such as extrusion. Some wetting agents, such as epoxidized soybean oils, also serve as secondary plasticizers. Examples of lubricants which can be used are stearates, stearic acid and low molecular weight polyethylene. These constituents can be used in a concentration of up to about 20% by weight of the total composition.

To produce the shaped articles according to the invention based on a vinyl resin the various constituents are mixed in the dry form by known mixing processes and the mixtures are molded by known extrusion or injection molding processes.

The choice of the processing method for production of the shaped articles according to the invention technically depends in principle on the rheological properties of the material of the shaped article and the shape of the desired structure. The processing methods can be formulated according to the processing technology or according to the nature of shaping. In the case of process technology, the methods can be subdivided according to the rheological states passed through during the methods. Accordingly, casting, pressing, injection and application are suitable for viscous shaped article materials, and injection molding extrusion, calendering milling and if appropriate canting are suitable for elastoviscous polymers. Classified according to the nature of the shaping, the shaped articles according to the invention can be produced by casting, dipping, pressing, injection molding, extrusion, calendering, embossing, bending, deep-drawing and the like.

These processing methods are known and do not require more detailed explanation. In principle, the explanations given above by way of example for polyvinyl resins apply to polymers such as polyamides and polyesters.

Agents which act by a systemic action via the haemolymphs of the insects are, for example, foods which contain the active compounds. Foods which may be mentioned are: sugar granules, sugar-containing mixtures, solutions, suspensions or emulsions. These contain active compound concentrations of 0.5–20% by weight, preferably 1–10% by weight. These mixtures are diluted further with water or sugar solution to use concentrations of the active compound of $10^{-8}-1\%$ by weight, preferably 0.0001–0.01% by weight and particularly preferably 0.0001–0.005% by weight.

Ready-to-use food pastes or doughs which contain the active compound in the use concentration, in addition to sugar and starch, may furthermore be mentioned.

Agents for use of the active compounds in drinking water are particularly preferred. Water-miscible solutions of the active compounds which contain one or more polar solvents and have an alkaline reaction are suitable here.

To prepare such solutions, the active compound is dissolved in a polar water-soluble solvent which either has an alkaline reaction or to which an alkaline water-soluble substance is added. The latter is advantageously also dissolved in the solvent, but can also be suspended in the solvent and dissolved only in the drinking water. The drinking water here should have a pH of more than 7, but preferably a pH of greater than pH 8 and less than 11, after addition of the active compound solution.

The drinking water can have a sugar content (glucose) of 0.1 to 5% by weight, preferably about 1% by weight.

The solution of the active compound concentrate should not exceed a pH of 11.

The concentration of the active compound can be in the range from 0.5 to 50%, but preferably in a range from 1 to 25%.

Possible solvents are all the water-soluble solvents in which the active compound is soluble in a sufficient concentration and which are physiologically acceptable.

These are, from the series of alcohols, mono and polyhydric alcohols, such as, for example, ethyl alcohol, isopropyl alcohol, benzyl alcohol, glycerol, propylene glycol, polyethylene glycols and poly(oxyethylene)-poly(oxypropylene) polymers, and basic alcohols, such as, for example, mono-, di- and triethanolamine.

Ketones, for example acetone or methyl ethyl ketone, and, from the series of esters, for example ethyl lactate, are also suitable. Other solvents, such as N-methylpyrrolidone, dimethylacetamide and dimethylformamide, can likewise be employed.

Bases which can be used for establishing the alkaline pH are preferably organic bases, for example basic amino acids, such as L- or D,L-arginine, L- or D,L-lysine, methylglucosamine, glucosamine, 2-amino-2-hydroxymethylpropane-1,3-diol, choline and piperazine. Diamines are also suitable here, for example N,N,N',N'-tetrakis-(2-hydroxypropyl)-ethylene-diamine or a polyether-tetrol based on ethylenediamine (molecular weight 480–420, OH index 432–467), also forms clear solutions in the pH range stated. Organic bases, for example ammonia or sodium carbonate, can also be employed—if appropriate with the addition of water.

Substances which are otherwise used as emulsifiers or solubilizers and are colloidally soluble in water can in this case be used in the same way as polar solvents if a basic auxiliary is also mixed with them.

To prepare the solutions, the substances are weighed into a vessel with a stirrer and are then stirred, with warming, until a clear solution has formed.

Water-miscible solutions of the active compounds for use in the drinking water are, for example:

EXAMPLE 1

2.5 g of toltrazuril are dissolved in triethanolamine to make up to 100 ml, with warming.

After dilution with water in a ratio of 1:10, the clear solution has a pH of 10.2.

EXAMPLE 2

2.5 g of toltrazuril and 12.5 g of lactic acid are dissolved in triethanolamine to make up to 100 ml, while warming and stirring.

After dilution of the solvent with water in a ratio of 1:10, the pH is 8.3.

EXAMPLE 3

10.0 g of toltrazuril are dissolved in monoethanolamine to make up to 100 ml.

After dilution with water in a ratio of 1:10, the clear solution has a pH of 11.

EXAMPLE 4

| | |
|---|---|
| Toltrazuril | 5.0 g |
| Propylene glycol | 50.0 g |
| Sodium carbonate | 5.0 g |
| Water to make up to | 100 ml |
| pH of the solution 9.9. | |

EXAMPLE 5

| | |
|---|---|
| Toltrazuril | 2.5 g |
| Sodium carbonate | 5.5 g |
| Polydiol 200 to make up to | 100 ml |

The active compound is dissolved in the polydiol and the sodium carbonate is suspended in the solution. PH of 9 after dilution with water in a ratio of 1:10.

Examples of formulations for spraying, which before use are diluted to the use concentration with water:

EXAMPLE 6

| | | |
|---|---|---|
| Toltrazuril | | 20 g |
| Emulgator Toximul ® | (Mixture of Ca alkylbenzene-sulphonate and non-ionic emulsifiers and methanol with a hydrophilic/lipophilic balance HLB value of 10) | 7 g |
| Emulgator Toximul S ® | (Mixture of Ca alkylbenzene-sulphonate and non-ionic emulsifier and methanol with a hydrophilic/lipophilic balance HLB value of 10) | 5 g |
| Solvesso 200 ® | (alkylnaphthalene mixture of high-boiling petroleum fractions) to make up to | 100 ml |

EXAMPLE 7

| | | |
|---|---|---|
| Toltrazuril | | 16 g |
| Emulgator 368 ® | alkylaryl polyglycol ether (molecular weight about 1165) | 9 g |
| Emulgator N P 10 ® | Nonylphenol polyglycol ether | 9 g |
| Dimethylformamide | | 10 g |
| Solvesso 200 | to make up to | 100 ml |

EXAMPLE 8

| | | |
|---|---|---|
| Toltrazuril | | 5 g |
| Emulgator Atlox ® | (Mixture of polyoxyethylene ether, polyoxyglyceride and alkylarylsulphonate - very readily water-soluble) | 4 g |
| Emulgator Atlox 3404 ® | (Mixture of polyoxyethylene alkylaryl ether, alkylaryl-sulphonate - forms an emulsion in water) | 2 g |
| Emulgator Atlox 3409 ® | (Mixture of non-ionic and anionic emulsifiers - soluble in water) | 4 g |
| Solvent PC 2 | (high-boiling aromatic petroleum fraction) to make up to | 100 ml |

EXAMPLE 9

| | | |
|---|---|---|
| Toltrazuril | | 1 g |
| Dowanol DPM ® | (Dipropylene glycol methyl ether) to make up to | 100 ml |

EXAMPLE 10

| | | |
|---|---|---|
| Active compound: | Toltrazuril | 0.5 g |
| Wetting agent: | Emulvin W ® (alkylaryl polyglycol ether) | 3.0 g |
| | Water to make up to | 100 ml |

An example of a dusting agent is:

EXAMPLE 11

1 g of toltrazuril is mixed thoroughly with 99 g of talc. 5 g of this mixture are mixed thoroughly with 95 g of talc.

Example of a PVC shaped article:

EXAMPLE 12

| | | |
|---|---|---|
| Toltrazuril | 0.5 | g |
| Isobutyl adipate | 15.5 | g |
| Dialkyl pythalate | 8.0 | g |
| Polyoxyethylated castor oil | 2.0 | g |
| Stearic acid | 0.8 | g |
| Dyestuff | 0.1 | g |
| Polyvinyl chloride | 73.1 | g |
| | 100.0 | g |

100.0 kg of this mixture are mixed homogeneously in a mixer—by the customary procedure for plasticized PVC.

This mixture is processed to a honeycomb partition on an injection molding machine. Weight of the partition: 86.0 g.

The above mixture is prepared with 0.5 instead of 0.25 g of active compound and is milled on an appropriate calendering device to a film the size of a DIN A4 sheet. Weight of the film 50.0 g. The sheet is placed, for example, in the beehive.

Example of a coated carrier:

EXAMPLE 13

A solution of toltrazuril in Emulgator Span 20® Atlas and ethanol is applied uniformly, by means of a doctor blade, to a 2 mm thick film of polyethylene. The solution is formulated so that 1 mg of toltrazuril per 100 $cm^2$ of surface and 0.5 mg of emulsifier per 100 $cm^2$ are applied. The solvent is evaporated off and the film is stamped into any desired shape.

Examples of an impregnated carrier with a polymer (=lacquer) additive:

EXAMPLE 14

Aluminum foil coated with kieselgur is treated with a solution of toltrazuril and polyvinyl alcohol so that, after drying, 5 mg of toltrazuril and 20 mg of polyvinyl alcohol per 100 $cm^2$ remain on the foil.

The carrier forms of the last two examples can be provided with an adhesive. After pulling off the protection for the adhesive, they can easily be stuck in insect habitats.

Example of granules for feeding:

EXAMPLE 15

0.5 kg of toltrazuril is dissolved in 7.5 l of ethanol, with careful warming, and the solution is poured onto 99.5 kg of sugar in a mixing granulator while the mixer is running. The alcohol-moist uniformly impregnated sugar is dried and if appropriate sieved. 1.0 g of the granules are dissolved before use in 100 ml of water to give a sugar solution which the insects use for food.

Example A:

10 adult hymenopters (*Pimpla turionella*) which were infested with *Nosema apis* were kept at 22° C. for 48 hours and treated ad libitum, via the drinking water, with a 1% strength sugar solution containing 20 ppm of toltrazuril.

At the end of the experiment, 9 animals were alive, and were sacrificed. Microscopic examination showed damage (in some cases cytolysis) to the parasitic protozoa on them.

In a control group treated only with sugar water (1% strength), 7 of the 10 animals died. The surviving animals were heavily infested by *Nosema apis.*

Example B:

Abdomen portions of *Pimpla turionella* which had first been examined microscopically for the presence of *Nosema apis* were placed in 30 ml of physiological sodium chloride solution containing 20 ppm of toltrazuril. After incubation at 20° C. for 12 hours, the parts were examined again under a light microscope. Severe damage to the protozoa was found. In a control without the active compound, no damage to the protozoa was to be found.

It will be understood that the specification and examples are illustrative but not limitative of the present invention and that other embodiments within the spirit and scope of the invention will suggest themselves to those skilled in the art.

What is claimed is:

1. A method of combating protozoa in insects which comprises applying to said infested insects an amount effective therefor of a triazinetrione of the formula

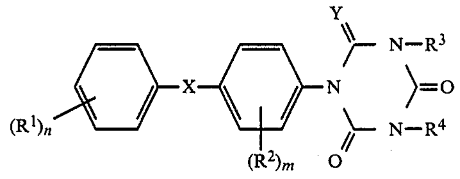

(I)

in which

X is O or S,

Y is O or S, $R^1$ and $R^2$ each independently is a radical selected from the group consisting of halogen, nitro, CN, amino, $C_{1-4}$-alkyl, $C_{1-4}$-halogenoalkyl, $C_{1-4}$-alkoxy, methylenedioxy, $C_{1-4}$-halogenoalkoxy, $C_{1-4}$-alkylthio, $C_{1-4}$-halogenoalkylthio, $C_{1-4}$-alkylsulphonyl, $C_{1-4}$-alkylsulphinyl, $C_{1-4}$-halogenoalkylsulphonyl, $C_{1-4}$-halogenoalkylsulphinyl, $C_{1-4}$-acyl, carboxy, carbonylamino, carbonyl-$C_{1-4}$-alkoxy, carbamoyl and sulphamoyl, n and m each independently is an integer from 0 to 3, and $R^3$ and $R^4$ each independently is hydrogen or $C_{1-4}$-alkyl.

2. The method according to claim 1, in which

X and Y each is O, $R^1$ and $R^2$ each independently is a radical selected from the group consisting of halogen, nitro, CN, amino, $C_{1-4}$-halogenoalkyl, $C_{1-4}$-alkoxy, methylenedioxy, $C_{1-4}$-halogenoalkoxy, $C_{1-4}$-alkylthio, $C_{1-4}$-halogenoalkylthio, $C_{1-4}$-alkylsulphonyl, $C_{1-4}$-sulphinyl, $C_{1-4}$-halogenoalkylsulphonyl $C_{1-4}$-halogenoalkylsulphinyl, $C_{1-4}$-acyl, benzoyl, and $C_{1-4}$-carbonylalkoxy, n and m each independently is an integer from 0 to 2, and $R^3$ and $R^4$ each independently is hydrogen or $C_{1-4}$-alkyl.

3. The method according to claim 1, in which $R^4$ is hydrogen, $R^3$ is $C_{1-4}$-alkyl, Y is O or S, X is O, $R^2$ each independently is a radical selected from the group consisting of $C_{1-4}$-alkyl, halogen, $C_{1-4}$-alkoxy and $C_{1-2}$-halogenalkyl, $R^1$ each independently is a radical selected from the group consisting of halogen; $NO_2$; $C_{1-4}$-alkyl; $C_{1-2}$- halogenoalkyl; $C_{1-4}$-alkylmercapto which is optionally substituted by halogen; $C_{1-4}$-alkoxy which is optionally substituted by halogen; $C_{1-4}$-alkylsulphinyl which is optionally substituted by halogen; and $C_{1-4}$-alkylsulphonyl which is optionally substituted by halogen; and n and m each independently is an integer from 0 to 2.

4. A method according to claim 1, in which $R^4$ is hydrogen, $R^3$ is methyl, X and Y each is O, $R^2$ is a radical selected from the group consisting of chlorine, bromine, methyl, trifluoromethyl, methoxy and ethoxy, $R^1$ is a radical selected from the group consisting of trifluoromethylmercapto, trifluoromethylsulphinyl, trifluoromethylsulphonyl and trifluoromethoxy, and n and m independently of one another are 0 or 1.

5. A method according to claim 1, wherein the triazinetrione is 1-[3-methyl-4-(4'-trifluoromethylthio phenoxy)-phenyl]-3-methyl-1,3,5-triazine-2,4,6(1H,3H,5H)-trione.

* * * * *

UNITED STATES PATENT AND TRADEMARK OFFICE
CERTIFICATE OF CORRECTION

PATENT NO. : 4,837,216

DATED : June 6, 1989

INVENTOR(S) : Mehlhorn et al

It is certified that error appears in the above-identified patent and that said Letters Patent is hereby corrected as shown below:

Col 12, line 49 After "amino, $C_{1-4}$" add -- -alkyl, $C_{1-4}$--

Col. 12, lines 51-52 After "alkylsulphonyl, $C_{1-4}$" add -- -alkyl--

Signed and Sealed this

Seventeenth Day of July, 1990

Attest:

HARRY F. MANBECK, JR.

*Attesting Officer* *Commissioner of Patents and Trademarks*